United States Patent
Abhari

(10) Patent No.: US 8,394,900 B2
(45) Date of Patent: Mar. 12, 2013

(54) PROFITABLE METHOD FOR CARBON CAPTURE AND STORAGE

(75) Inventor: Ramin Abhari, Bixby, OK (US)

(73) Assignee: Syntroleum Corporation, Tulsa, OK (US)

( * ) Notice: Subject to any disclaimer, the term of this patent is extended or adjusted under 35 U.S.C. 154(b) by 385 days.

(21) Appl. No.: 12/727,014

(22) Filed: Mar. 18, 2010

(65) Prior Publication Data
US 2011/0230632 A1    Sep. 22, 2011

(51) Int. Cl.
*C08F 2/00* (2006.01)
*C10G 57/02* (2006.01)
*C08F 10/02* (2006.01)

(52) U.S. Cl. .......... 526/75; 527/103; 585/240; 585/242; 585/327; 585/648; 208/71; 208/950; 44/605; 44/606

(58) Field of Classification Search .................. 526/75; 585/240, 242; 527/103; 208/71, 950; 44/605, 44/606
See application file for complete search history.

(56) References Cited

U.S. PATENT DOCUMENTS
6,660,812 B2 * 12/2003 Kuechler et al. ............... 526/68
7,288,685 B2 * 10/2007 Marker .......................... 585/240

FOREIGN PATENT DOCUMENTS
WO    WO 2008/067627 A2 *  6/2008

* cited by examiner

*Primary Examiner* — Fred M Teskin
(74) *Attorney, Agent, or Firm* — Hall Estill Law Firm

(57) ABSTRACT

The present invention generally relates to a method for sequestering carbon dioxide. Biomass is converted into paraffinic hydrocarbons. The paraffinic hydrocarbons are steam cracked into olefins. The olefins are polymerized into non-biodegradable polyolefins.

17 Claims, 1 Drawing Sheet

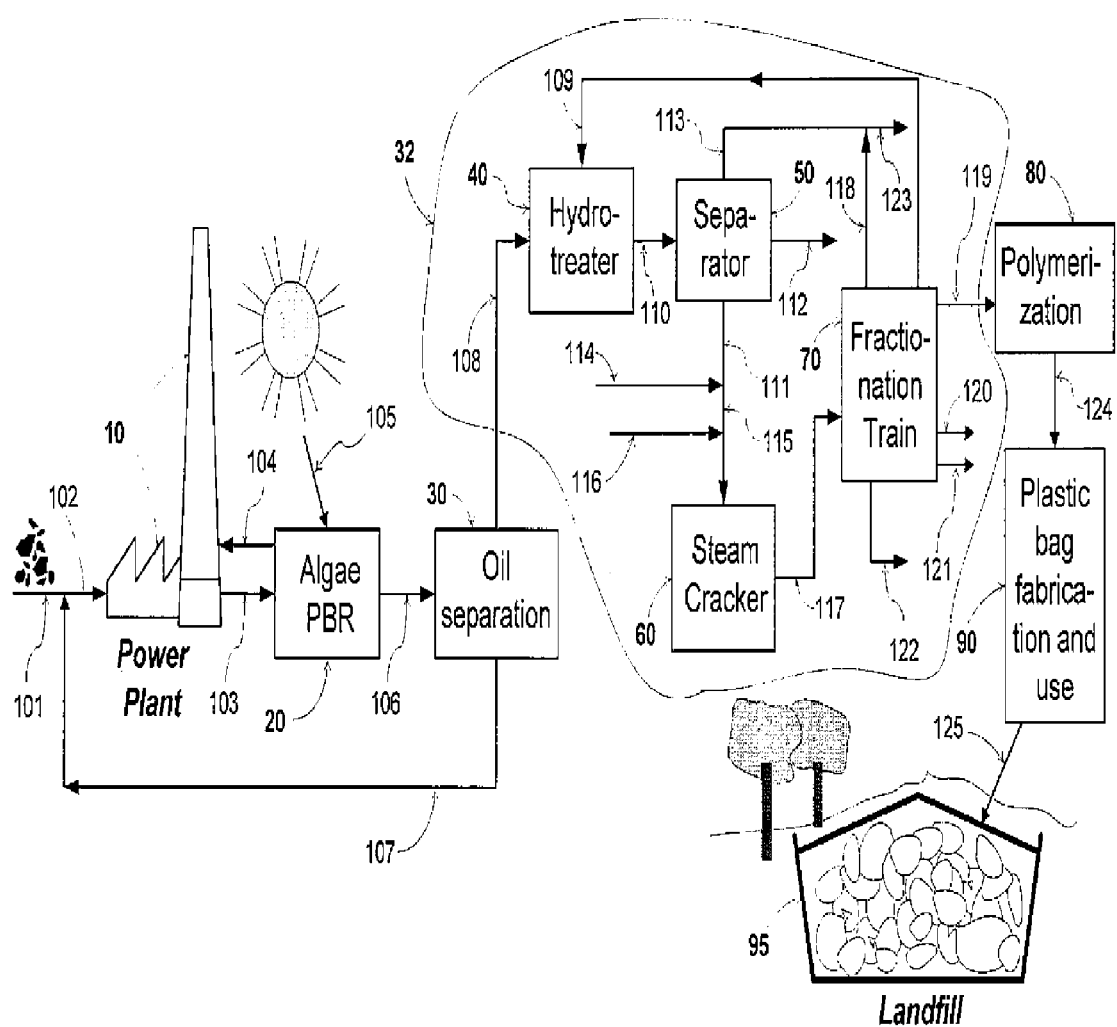

PROFITABLE METHOD FOR CARBON CAPTURE AND STORAGE

CROSS REFERENCE TO RELATED APPLICATIONS

Not applicable.

FEDERALLY SPONSORED RESEARCH

Not applicable.

FIELD OF THE INVENTION

The present invention relates to a method for sequestering carbon dioxide. The present invention also relates to a process for producing bio-based olefins, polyolefins, and motor gasoline.

BACKGROUND OF THE INVENTION

There is a growing consensus among climate scientists that the increasing concentration of heat trapping carbon dioxide ($CO_2$) in the atmosphere—mainly from combustion of fossil fuels—is contributing to global warming. Consequences of global warming include melting of polar ice caps and rising sea levels, threatening arctic ecosystems and endangering coastal communities.

Climate scientists argue that during most of human history—up to the industrial revolution—the air held no more than 275 ppm $CO_2$. The atmospheric $CO_2$ concentration in 2009 was 385 ppm and rising. To slow down global warming, $CO_2$ from high fossil fuel emission sources such as coal-fired power plants, needs to be captured and "returned" to the ground—essentially reversing the fossil fuel mining, processing, and combustion process.

A number of $CO_2$ capture and storage (CCS) technologies have been developed. The storage of $CO_2$ has also been referred to as $CO_2$ sequestration. One method for CCS uses metal oxide solutions, such as potassium or magnesium oxide, to remove $CO_2$ from flue gas or other $CO_2$ containing vent gases. The general capture mechanism involves reaction of the metal oxides with $CO_2$ to form metal carbonates. These carbonate salts can either be land-filled, or be regenerated via oxidation to form a concentrated $CO_2$ stream that can be compressed and injected into geological formations for storage.

Conventional gas absorption units, commonly referred to as scrubbers, may be used to remove $CO_2$ from flue gas using the metal oxide solutions as absorption liquids. Other $CO_2$ absorption liquids include amine systems. With amine systems, the absorption liquid is typically regenerated and a concentrated $CO_2$ stream is formed for compression and in ground storage.

Although these gas absorption methods are technically mature, their use in CCS applications has been limited. This is in part due to the fact that not all geological formations are well-suited for $CO_2$ storage. Perhaps more importantly, the hesitation to adopt such CCS processes stems from the fact that the investment and operating cost for capture, compression and storage of $CO_2$ brings the carbon emitting plant owner no corresponding financial return.

Biomass burial and ocean storage have also been proposed for carbon sequestration. In the biomass burial and ocean storage approach, the carbon capture occurs naturally through photosynthesis, wherein sunlight and $CO_2$ combine to form carbonaceous biomass. However, the efficiency and effectiveness of this approach has been questioned. Unless stored under a controlled environment underground, the biomass is likely to decompose and re-release the $CO_2$. In certain environments, the biomass may undergo anaerobic decomposition into methane which has been reported to have a heat trapping efficiency 23 times higher than $CO_2$. Furthermore, as in the case of other prior art CCS processes, there is little economic incentive for adoption of this method.

More recently, algae growth and harvesting technologies have been adapted to carbon capture systems and apparatuses. Since algae growth is typically limited by rate of $CO_2$ supply, algae ponds and bioreactors have been designed to remove $CO_2$ from stationary emission sources. US patent publications 2007/0048848 and 2009/0162922 describe such systems, apparatus, and methods. In some embodiments, $CO_2$ rich flue gas from a coal-fired power plant is directed to an algae photo-bioreactor, where it undergoes photosynthetic conversion algal biomass. However, like terrestrial plants, algae are biodegradable. Upon decomposition, the fossil fuel-based $CO_2$ is released into the atmosphere. Consequently, a profitable and effective method of $CO_2$ capture and storage is needed.

One aspect of the present invention is production of bio-based polyolefins, basic chemicals, and hydrogen. Bio-based ethylene may be obtained from dehydration of ethanol. More recently, U.S. Pat. No. 7,288,685 has reported that olefins may be obtained by fluidized catalytic cracking of vegetable oils—although at lower yields than from steam cracking of hydrocarbons. However these processes require construction of new and expensive plants. Furthermore, these olefin production routes are not believed to be competitive with steam cracking of hydrocarbons, which is the technology used in all world scale olefin plants today. Consequently, a method of producing bio-based olefins utilizing existing steam crackers is desired.

Another aspect of the present invention is the production of bio-based motor gasoline components, suitable for use as spark-ignition engine fuels. Although the biofuel prior art provides various methods and systems for producing such compositions, the prior art methods and systems do not address early adoption issues such as capital costs for building new plants. By providing a method wherein existing petrochemical plants can be used to produce such fuels, the present invention addresses this important need.

SUMMARY OF THE INVENTION

A method for capture and storage of $CO_2$ is described herein. The invention is capable of being adapted for co-production of bio-based gasoline. An embodiment of the described method includes (a) photosynthetic conversion of $CO_2$ into biomass, (b) conversion of biomass to paraffinic hydrocarbons, (c) cracking the paraffinic hydrocarbons into olefins in a steam cracker, and (d) polymerization of the light olefins into polyolefin plastics. Polyolefins such as polyethylene and polypropylene are the most widely used plastics in the world, with annual production well over 125 million metric tons. These plastics are 86% carbon by weight, non-biodegradable, and a major component of the world's landfills. If produced by the method described herein, each ton of carbon in the plastic would represent 3.67 tons of $CO_2$ removed from the atmosphere, stored within useful products, and ultimately sequestered in commercial landfills. Furthermore, the present method of carbon capture and storage is inherently market friendly and builds on existing manufacturing infrastructure.

The CCS method of the present invention also produces bio-based gasoline, hydrogen, and basic chemicals.

BRIEF DESCRIPTION OF THE DRAWING

The drawing depicts a process for sequestering $CO_2$ generated from combustion of coal, according to one embodiment of the invention.

DETAILED DESCRIPTION OF THE INVENTION

The term "biodegradable" refers to a natural or synthetic chemical that can undergo aerobic or anaerobic decomposition into $CO_2$, $CH_4$, and other green house gases. The term "non-biodegradable" refers to synthetic chemicals that do not undergo aerobic or anaerobic decomposition into green house gases.

The terms "olefins" and "alkenes" refer to unsaturated hydrocarbons such as ethylene, propylene, 1-butene, cis- and trans-2-butene, and 1,3-butadiene. The term "polyolefin" refers to polymers and copolymers of these olefins.

The term "paraffinic hydrocarbon" refers to a composition containing mostly alkanes and iso-alkanes (also called paraffin and iso-paraffin respectively). Such compositions contain about 30 to 100 wt % n-paraffins, about 0 to 80 wt % isoparaffins, less than about 10 wt % cycloparaffins (also referred to as naphthenics), less than about 5 wt % olefins, less than about 1 wt % aromatics, and less than about 0.5 wt % elemental oxygen, sulfur, and nitrogen.

The term "$C_x$", where x is a number greater than zero, refers to a hydrocarbon compound having predominantly a carbon number of x. As used herein, the term $C_x$ may be modified by reference to a particular species of hydrocarbons, such as, for example, $C_5$ olefins. In such instance, the term means an olefin stream included predominantly of pentenes but which may have impurity amounts, i.e. less than about 10%, of olefins having other carbon numbers such as hexene, heptene, propylene, or butene.

It has surprisingly been found that paraffinic hydrocarbons derived from biomass can be converted to olefins in conventional steam crackers with yields the same as or higher than petroleum fractions of similar boiling range, thus providing an economical route to bio-based polyolefins—a marketable product that sequesters atmospheric CO2. Furthermore, it has been observed that the gasoline fraction produced from steam cracking the bio-based paraffinic hydrocarbon is relatively low in low-octane n-paraffins, and high in high-octane aromatics, despite the fact that the bio-based paraffinic hydrocarbon feed is mainly n-paraffin and virtually free of aromatics. This discovery led to the present invention disclosed herein for sequestering photosynthesized $CO_2$ into useful and profitable products. As a result, the transition to a sustainable industrial production can be achieved sooner, without economic hardship, and while enhancing living standards around the world.

In some embodiments of the present invention the biomass produced via photosynthetic conversion of atmospheric $CO_2$, given by Equation 1, is wood chips and other cellulosic biomatter (denoted as $[CH_2O]_n$).

$$2nCO_2 + 2nH_2O + \text{sun light} \rightarrow 2[CH_2O]_n + 2nO_2 \quad (1)$$

The biomass feedstock is gasified to syngas, a gas composition comprising hydrogen and carbon monoxide, according to Equation 2.

$$2[CH_2O]_n + \tfrac{1}{2}O_2 \rightarrow 2nH_2 + nCO + nCO_2 \quad (2)$$

As observed from Equation 2, gasification is a partial oxidation reaction. Gasifiers differ in flow pattern (counter-current, co-current, or back-mixed), mechanical construction, and operating pressures (0 to about 500 psig). The oxygen for the Equation 2 reaction may be provided via compressed air or from an air separation unit. The common element in all gasifiers is high temperature—typically greater than about 1,250° F. After adjusting the $H_2$:CO ratio via water gas shift to between about 1.9:1 and about 2.2:1, preferably to about 2.1:1, the syngas is converted to hydrocarbons via Fischer-Tropsch (Fr) conversion. The conversion of syngas to FT hydrocarbons (denoted as $[—CH_2—]_n$), is given by Equation 3.

$$2nH_2 + nCO \rightarrow [—CH_2—]_n + nH_2O \quad (3)$$

For typical FT reactions, the paraffinic hydrocarbon product composition is given by n=2-100, with most paraffins in the 5 to 50 carbon number range. $CO_2$, nitrogen, and light hydrocarbons that are typically present in the syngas are generally inert at FT conversion conditions. Ammonia, hydrogen cyanide, nitrogen oxides, hydrogen sulfide, halides, and vapor phase organometallic compounds are preferably removed from syngas to improve FT catalyst activity. It should be understood that any of the methods and/or apparatuses known to persons having ordinary skill in the art, such as absorption columns (scrubbers) and/or adsorption beds, may be used to pretreat FT syngas. Low temperature methanol (Rectisol®) is a common absorption process for syngas cleanup, while zinc oxide and carbon beds are typical adsorption technologies for the same.

In one embodiment, the FT process operates under conditions that maximize formation of paraffinic hydrocarbons. Non-limiting examples of such processes are those utilizing cobalt-based syngas conversion catalysts. Cobalt FT catalysts may be supported on alumina, silica, titania, and/or zirconia and include other Group VIII metals, such as Ru, Rh, or Pd, as modifiers, and magnesium, potassium or lanthium as promoters. The FT reactions with high paraffin selectivity typically operate at pressures in the range of about 250 to about 600 psig and temperatures in the range of about 300 to about 500° F. Such FT conversions may be conducted in slurry or fixed-bed reactors. In the slurry reactors, the catalyst is typically suspended in the paraffinic wax reaction product by the dispersion of the syngas in the reactor. The heat generated by the exothermic FT reaction is removed using coils immersed in the slurry reactor. The flow regime in the slurry reactor is conducive to efficient heat removal through the coil-slurry heat transfer surface. The relatively low FT reactor temperature is thus controlled via water evaporation in the cooling coils. In the fixed-bed FT reactors, catalyst is packed in tubes of a multi-tube reactor apparatus. Heat is removed through water evaporation in the reactor shell containing the tubes.

In an alternate embodiment, the biomass produced by photosynthetic conversion of $CO_2$ includes oil-rich and fast growing seeds like rapeseed, jatropha, camelina, and soybean. The oil, mainly triglycerides of $C_{12}$-$C_{22}$ fatty acids, is separated by seed pressing or via solvent extraction. The seed press essentially squeezes out the oil from the rest of the biomass (meal). Hexane is typically used as solvent for oil extraction. The ratio of hexane to oil is in the 1:1 to 5:1 range. The hexane is then stripped from the oil and recycled to the extractor. Typically about 1-2% fresh hexane is required to make up for losses.

In other embodiments, the biomass produced by photosynthetic conversion of $CO_2$ includes grass and seeds that are consumed by cows, chicken, and other herbivores, and metabolized as animal fat. Enzymes in animal fats can catalyze the hydrolysis of triglycerides into free fatty acids and smaller esters (e.g. di- and mono-glycerides). Depending on processing conditions, this type of hydrolysis can occur in other bio-oils as well. In another embodiment, the biomass produced by photosynthetic conversion of $CO_2$ (Equation 1) includes photosynthetic organisms such as algae. In one embodiment, the algae are grown in a photo-bioreactor (PBR) or an algae pond wherein $CO_2$ is supplied from an adjacent facility burning fossil fuels. The $CO_2$ in the flue gas is converted to algal biomass in the PBR. Algae have been reported to include 20-40% oil, similar to oil bearing seeds. After dewatering and/or drying the algae using methods and apparatus known to those skilled in the art, including microfiltration membranes and/or spray dryers, oil may be recovered from algae using the same methods developed for seed oils and described previously herein.

The plant-based oils, animal fats, and/or algal oils are then directly converted to paraffinic hydrocarbons via hydrotreating. Hydrotreating is a term used in the petroleum refining industry to describe the series of reactions that occur when contacting a liquid feed with hydrogen over a heterogeneous hydrogenation catalyst. These reactions include saturation of double bonds and removal of heteroatoms. The hydrotreating catalysts for conversion of fatty acids and glycerides to paraffinic hydrocarbons are typically metal sulfide catalysts including Group VIII and Group VIB metals on oxides of aluminum, silicon, and/or phosphorus. Preferred hydrotreating catalysts for conversion of fatty acid glycerides to paraffinic hydrocarbons are nickel-tungsten, nickel-molybdenum, and cobalt-molybdenum. However, it should be understood to one of ordinary skill in the art that any catalyst for hydrotreating may be utilized so long as the catalyst functions in accordance with the present invention as described herein. In addition to hydrogenation of unsaturated fatty acids, hydrotreating removes oxygen—producing water via hydrodeoxygenation (Equation 4) and/or carbon oxides via decarboxylation (Equation 5). In one embodiment of the hydrotreating step, an adiabatic fixed-bed reactor is operated at about 400 to about 800° F., under $H_2$ partial pressure of about 200 to about 4,000 psia. In general, the hydrodeoxygenation reaction (Equation 4) is favored at higher hydrotreater pressures and the decarboxylation reaction (Equation 5) favored at lower pressures within the range. (Note that in Equations 3 and 4 oleic acid is shown as a typical fatty acid component of the bio-based oil, converting to n-octadecane and n-heptadecane respectively.)

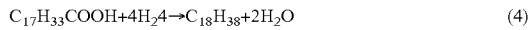
$$C_{17}H_{33}COOH + 4H_2 \rightarrow C_{18}H_{38} + 2H_2O \qquad (4)$$

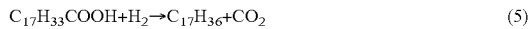
$$C_{17}H_{33}COOH + H_2 \rightarrow C_{17}H_{36} + CO_2 \qquad (5)$$

Under typical operating conditions, both types of reaction occur in the hydrotreater, thus converting the bio oil into a paraffinic hydrocarbon composition, water, CO, $CO_2$, and propane (from the glycerol backbone of fatty acid glycerides).

The hydrotreater is operated with a liquid hourly space velocity (LHSV) between about 0.1 and about 10 vol oil/vol catalyst/hr, and a gas-to-oil ratio (GOR) between about 3,000 and about 20,000 SCF/Bbl. Preferred LHSV and GOR are about 0.5-5 and about 4,000-10,000 respectively.

In some embodiments, the hydrotreater feed is combined with a hydrocarbon diluent/solvent. Since the catalyst is sulfided, some embodiments provide a sulfur component to maintain the hydrotreater catalyst in the desired active metal sulfide form.

The bio-derived paraffinic hydrocarbons from FT conversion (Equation 3) and/or hydrotreating (Equations 4 and 5) are about 30 to about 100 wt % n-paraffins, 0 to about 80 wt % isoparaffins, less than 10 wt % cycloparaffins, less than 5 wt % olefins, less than 1 wt % aromatics, and less than 0.5 wt % elemental oxygen, sulfur, and nitrogen. A typical bio-based paraffinic hydrocarbon contains about 90 wt % n-paraffins, about 8 wt % isoparaffins, about 2 wt % cycloparaffins and olefins, and less than 0.1 wt % aromatics and heteroatoms.

The bio-derived paraffinic hydrocarbon is processed through a conventional steam cracker to produce bio-based olefins and bio-based hydrogen. The illustrative cracking reaction of n-octadecane to ethylene is given by Equation 6. (Note that n-octadecane is a component of the paraffinic hydrocarbon product derived from bio oil hydrotreating, as illustrated by Equation 4, and of FT conversion, as given by Equation 3 for n=18.)

$$C_{18}H_{38} \rightarrow 9C_2H_4 + H_2 \qquad (6)$$

The conventional steam cracker includes furnaces in parallel. The feed is heated to temperatures in the about 1200° F. to about 1800° F. range (preferably about 1500-1600° F.) in the furnace tubes as it travels at high velocities before being quenched in a transfer line heat exchanger. The residence time is minimized, typically in the about 0.005 to about 5 second range, preferably about 0.01 to about 1 second. The low pressures, from about 10 to about 50 psia, promote the cracking reaction. This, along with low residence times, ensures that the olefins produced do not react as they travel through furnace tubes to the quench exchanger. The weight ratio of steam diluent to hydrocarbon, also referred to as dilution ratio, is between about 0.1 and about 10, preferably between about 0.2 and about 1. Under these conditions, the hydrocarbons are cracked mainly into $C_2$-$C_4$ olefins, hydrogen, methane, and ethane.

In addition to light olefins for polyolefin production, steam cracking of petroleum-based liquids also produces a C5+ hydrocarbon composition rich in olefins and aromatics. The $C_5$-$C_9$ fraction from the steam cracker is referred to as pyrolysis gasoline, and the $C_{10}$+ fraction as pyrolysis fuel oil. It has surprisingly been observed that steam cracking of bio-derived paraffinic hydrocarbons, unlike petroleum-based feeds of the same boiling range, produces virtually no pyrolysis fuel oil and thus a higher yield of the lighter olefins.

At the high temperatures used for steam cracking, the tube metal can catalyze steam-reforming of some of the light hydrocarbon products. This is generally an undesirable reaction since it reduces light olefin yield. This tube metal catalyzed reaction is inhibited by presence of sulfur in the feed. Since the bio-based paraffinic hydrocarbons are very low in sulfur, addition of sulfur either by blending with a sulfur containing petroleum fraction or with a sulfur additive like dimethyl disulfide may be desirable. On the other hand, too much sulfur also inhibits the desired decoking reactions that occur naturally with steam in the furnace tubes. As such, by blending bio-based paraffinic hydrocarbons with petroleum-based feeds, the steam cracker operator is able to better optimize unit performance, achieving higher light olefin yields and longer run lengths than by using petroleum-based feeds alone.

The quenched steam cracker effluent is transferred to a fractionation train wherein the gas phase products are separated from the pyrolysis gasoline. The gas phase products are compressed and fractionated into hydrogen, fuel gas, ethylene, propylene, and C4 olefins. The hydrogen is typically a major component of a hydrogen-rich gas, wherein hydrogen concentration is about 70 to about 99 mol %, with methane comprising the main impurity. The separated methane, ethane, and smaller amounts of $C_3$-$C_4$ paraffinic byproducts, are primarily used as plant fuel. It should be noted that steam cracking is an endothermic process in need of fuel. The bio-derived fuel gas components obtained from blending bio-based paraffinic hydrocarbons in the steam cracker feed thus offers the olefin plants a way of reducing their fossil-based CO2 emissions while practicing the teachings of this invention.

Polymerization of ethylene to polyethylene is shown in Equation 7.

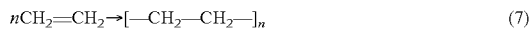

$$nCH_2{=}CH_2 \rightarrow [{-}CH_2{-}CH_2{-}]_n \qquad (7)$$

For polymerization, ethylene and propylene streams with purities of equal to or greater than 94 mol %, preferably equal to or greater than 98 mol %, are used. The ethylene and propylene may be transported via pipeline to ethylene and propylene polymerization plants. Therein polyolefin pellets are produced which may later be physically transformed into many useful plastic products.

Polyethylene is generally classified into low density (LDPE, 0.91-0.94 g/cm$^3$), high density (HDPE, $\geq$0.941 g/cm$^3$), and linear low density (LLDPE, 0.915-0.925 g/cm$^3$). LDPE is commercially produced by free radical polymerization of ethylene in high pressure tubular or autoclave reactors. These reactors are operated at high pressures to ensure the polymer/ethylene system is single phase at high temperatures required for free radical polymerization. The high pressure process uses reactor temperatures in the about 280° F. to about 670° F. range, and pressures in the about 17,000 psig to about 45,000 psig range. The polymer product has a high degree of short and long chain branching, which results in a lower tensile strength and increased ductility. Residence times for high pressure polyethylene reactors are typically in the 15 seconds to 2 minute range. Polymerization is initiated by oxygen, or by peroxides such as tert-amyl perneodecanoate and benzoyl peroxide. Per pass conversions are typically in the 15% to 40% range. Molten LDPE from reactor is separated from unconverted ethylene in high and low pressure separators. Unconverted ethylene is recycled to the reactor while LDPE is extruded to disperse additives, and pelletized. Preferred equipment for LDPE pelletizing includes strand pelletizer and underwater pelletizer systems.

Compared to LDPE, HDPE has a higher degree of crystallinity and short chain branching. It is produced via Ziegler-Natta (e.g. TiCl$_3$ or VCl$_3$), chromium oxide (CrO$_3$ on silica), or single-site (e.g. metallocenes) catalysts which enable polymerization at lower reactor temperatures compared to the free radical initiated reaction. HDPE processes employ solution, slurry (e.g. loop reactors), and gas phase (e.g. fluidized-bed) reactor designs. Comonomers such as C$_4$-C$_8$ linear alpha olefins may be added to these reactors to produce LLDPE grades.

In the solution process, the reaction solvent, typically Isopar®, cyclohexane, or n-hexane, is flash separated and recycled to the continuous stirred tank reactor. The molten polymer from flash separation and/or devolatilization is then processed through a gear pump and/or extruder for pelletizing.

In the slurry process, the liquid diluent includes a light hydrocarbon such as isobutane. The HDPE particles produced are kept in suspension by recirculation at high velocities. The polymer powder is separated from light hydrocarbon vapor. The light hydrocarbon diluent is recompressed and recycled to the reactor while the polymer powder is transferred to an extruder (typically a twin-screw) where it is melted, additized with an anti-oxidant system, and pressurized through a die for pelletizing.

In the gas phase process, the polymer powder is separated from the monomer vapors in a cyclone. The vapor phase is compressed and recycled to the reactor while the polymer powder is melt processed through an extruder and pelletized, typically with an anti-oxidant. For polyolefin stabilization, phosphite anti-oxidants are commonly used. Anti-oxidant blends, using combinations of phosphites, hindered phenols, hydroxylamines, Vitamin-E, and other stabilizers may also be used for the purpose of protecting the plastic from discoloration and/or molecular weight distribution change as it is further processed through plastic processing equipment. Ethylene polymerization is highly exothermic. All reactor designs discussed include provisions for temperature control.

Polyethylene is used in many applications that take advantage of its low weight, chemical resistance, cost, and ease of forming via extrusion, blow molding, injection molding, and other polymer processing operations—and new applications for this versatile plastic are developed every year. According to Wikepedia.com, HDPE end-uses include, but are not limited to, telecom ducts (underground cable conduits), containers (e.g. laundry detergent bottles, milk jugs, and fuel tanks), plastic lumber, furniture (e.g. folding tables and chairs), storage sheds, support bases for portable basketball systems, playground slides, plastic bags, geo-membranes for hydraulic applications (canals, bank reinforcements, etc.) and chemical containment, geothermal heat transfer piping systems, natural gas distribution pipe systems, water pipes, corrosion protection for steel pipes, Tyvek™ (non-woven HDPE fabric), snow boards, hula hoops, ballistic plates/caps, and bottles.

LDPE is used for trays and general purpose containers, food storage and laboratory containers, corrosion-resistant work surfaces, six-pack can rings, computer components (e.g. hard-drives, screen cards, and disk-drives), plastic bags, and plastic wraps.

LLDPE may be used for most of the above applications in addition to polymer film/sheet applications where a lower thickness is desired. Plastic wrap and stretch wrap, pouches, toys, covers, lids, buckets, cable covering and flexible tubing constitute some of the main LLDPE applications.

Propylene, the second most important olefin from steam cracking of bio-based paraffinic hydrocarbons, may be polymerized in slurry or gas phase. Examples of slurry polymerization systems, wherein the polymer particles are suspended in monomer liquid at steady-state conditions, include stirred tank and loop reactors. The gas phase process is typically a fluidized bed reactor system wherein the polymer particles are suspended in monomer vapor. Both Ziegler-Natta and metallocene catalyst/activator systems may be used for polypropylene production. Most catalyst and reactor systems are designed to produce isotactic polypropylene (iPP), a high crystallinity rugged thermoplastic. After separation of iPP powder from propylene monomer vapors and monomer recycle, the powder is extruded and pelletized. Just like polyethylene, polypropylene needs to be stabilized with an anti-oxidant.

Polypropylene may be injection molded, blow molded, extruded, and spun into many different articles. It has a better resistance to mechanical fatigue and chemicals than polyethylene and has been used in some engineering thermoplastic applications where tight tolerances are required (e.g. for threaded bottle caps and those with flip-top spout closures). Other examples of polypropylene applications include, but are not limited to, packaging (including see-through plastic molding), textile (e.g. ropes, thermal underwear, and carpets), non-wovens (diapers, dust masks), kitchenware (e.g. many household Tupperware® and Rubbermaid® products), laboratory equipment (where acid resistance is required), and automotive components. When copolymerized with ethylene, the crystallinity of the polypropylene is diminished and it becomes rubbery. Diene modified ethylene-propylene rubber (EPDM) can be used in many high temperature hose applications (e.g. car engine systems). EPDM is compounded with iPP to improve the latter's low temperature impact resistance. Impact modified polypropylene is used as car bumper.

In addition to polypropylene, propylene derivatives include isopropanol (IPA), acrylonitrile, oxo alcohols, cumene, and $C_3$ oligomers ($C_6$, $C_9$, and $C_{12}$ branched olefins). IPA and $C_6$-$C_9$ propylene oligomers may be used as gasoline blend stocks. (Oligomerization conditions are described in more detail in the C4 mono-olefin paragraph below.)

The $C_4$ olefin stream, the third major olefin stream from steam cracking the bio-based paraffinic hydrocarbons, is direct to a 1,3-butadiene extraction unit. Extraction solvents for separation of butadiene from $C_4$ mono-olefins include acetonitrile, N-methylpyrrolidone, and dimethyl formamide. Butadiene is used for production of polymers such as polybutadiene rubber, styrene-butadiene rubber, and acrylonitrile-butadiene-styrene engineering plastic.

In some embodiments, the 1,3-butadiene is converted to $C_4$ mono-olefins by selective hydrogenation. Selective hydrogenation typically uses Pd on alumina catalyst at temperatures in the 100 to 300° F. range under 100 to 1000 psia $H_2$ partial pressure.

The $C_4$ mono-olefins, remaining in the $C_4$ olefin stream after butadiene extraction and/or selective hydrogenation, include isobutylene, 1-butene, and cis/trans-2-butene. Like propylene, this stream may be subjected to oligomerization alone or along with the propylene to produce a highly branched hydrocarbon composition known as polymer gasoline (also referred to as polygas for short). Presence of 1-butene in the oligomerization feed increases the octane rating of polygas, making it suitable for use as a gasoline blend stock even after it has been hydrogenated and olefins therein saturated. Depending on oligomerization conditions, product carbon number distribution may include components suitable for use as jet fuel and diesel as well as gasoline. Oligomerization reactions are typically conducted over fixed bed catalysts including solid phosphoric acid and zeolites. Typical reaction conditions are about 350 to about 450° F., and about 400 to about 1,000 psig. The carbon number distribution (and hence fraction of fuel in gasoline vs. jet/diesel range) is shifted with temperature; higher temperatures yielding more gasoline. For temperature control, both multi-tube fixed bed reactors with direct heat exchange, and adiabatic fixed bed reactors with high product recycle ratios and/or multiple quench zones are used.

In an alternative embodiment, the isobutylene in the mixed C4 mono-olefin stream is subjected to acid catalyzed hydration, producing tert-butyl alcohol which is considered a superior oxygenate for motor gasoline—with a higher octane rating than n-butanol. The removal of isobutylene does not change the suitability of the 1-butene and cis/trans-2-butene components for conversion to polygas.

Pyrolysis gasoline stream obtained from steam cracking of the bio-based paraffinic hydrocarbons contain mainly $C_5$-$C_{10}$ olefins, aromatics, and naphthenic functional groups. This is hydrogenated to remove the diolefin gum-formers before blending with other gasoline components, such as the polygas composition and/or the alcohols derived from acid-catalyzed hydration of light olefins, as described in the previous paragraphs herein. Surprisingly, despite the fact that the bio-derived paraffinic hydrocarbon feed to the steam cracker is mostly n-paraffins and virtually free of aromatics, the pyrolysis gasoline derived from this feed, includes about 30 to about 50 wt % aromatics with only about 5 to about 20 wt % n-paraffins. As such, the pyrolysis gasoline product of this invention is a suitable gasoline blend stock, and very similar to petroleum derived gasoline fractions.

An embodiment of the present invention is schematically represented in the drawing. The embodiment is based on adding facilities to an existing coal fired power plant and an existing olefin plant to achieve carbon capture and sequestration by the method of the present invention. Referring now to one embodiment of the method in the drawing, coal 101 is combusted in the boilers of power plant 10. The $CO_2$-containing flue gas 103 from coal combustion is directed from the power plant 10 to a water-circulation photo-bioreactor (PBR) 20 where the $CO_2$-containing flue gas 103 undergoes photosynthesis with sunlight 105 to produce algae 106, and an exiting flue gas 104 having a diminished $CO_2$ concentration. In one mode of operation, about 40% to about 80% of the. $CO_2$ generated by combustion of coal is photosynthesized in the PBR 20.

Water from the PBR 20 may be brackish water or fresh water. The pH of the PBR 20 is maintained high to increase the solubility of $CO_2$ in water. As such, night time $CO_2$ emissions build up in the PBR 20 for photosynthetic conversion during daylight. In some embodiments, the bioreactor pH may be cycled between night and day operations to optimize average $CO_2$ removal. In some embodiments, instead of the PBR 20, the $CO_2$ may be photosynthesized with an algae pond.

The PBR 20 is also equipped with equipment for dewatering and drying the algae, such as microfiltration membranes and spray dryers. Availability of large volumes of hot flue gas 103 from the boiler of the power plant 10 provides operational synergies between the power plant 10 and the PBR 20. For example, the hot flue gas may be used to spray dry the algae stream exiting the PBR 20 before the gas is fed to the PBR 20.

The algae 106 is fed into an oil separator 30 which includes an extractor and a stripper. Hexane extraction is used to separate the oil 108 from the remaining algae biomass or meal 107. Hexane is then stripped from the recovered oil and recycled to the extractor. The ratio of hexane-to-oil is in the 1:1 to 5:1 range. Typically about 1-2% fresh hexane is required to make up for losses. An alternative method of separating oil from algae is a press. The press method essentially squeezes out the oil from the remaining biomass.

In the embodiment of the drawing, the power plant 10, the PBR 20 and the separator 30 are located at the same plant site. The algal meal 107 is used to supplement the coal blend 102 fed to the boiler(s) of the power plant 10. In other embodiments, particularly when the oil separator 30 is not co-located with the power plant 10, the algae meal may be used as animal feed. Other uses for the algae meal include gasification and synfuel production. It should be understood by one of ordinary skill in the art that various parts and equipment described in the present invention may be located in the same location or in different locations wherein the effluents/products are transported as needed, so long as the various parts and equipment function in accordance with the present invention as described herein.

The algal oil produced from photo-conversion of coal-based $CO_2$ is transported to an olefin plant 32. The olefin plant 32 includes a hydrotreater 40, a separator 50, a steam cracker 60, and a fractionator 70. Algae oil 108 is fed into the hydrotreater 40 where the algal oil 108 reacts with the hydrogen in hydrogen-rich treat gas 109. The hydrotreater 40 includes equipment for heating and contacting the algal oil with a hydrotreating catalyst, such as nickel-tungsten, nickel-molybdenum, cobalt-molybdenum, or the like as discussed herein. In one embodiment, the hydrotreater 40 is a fixed-bed reactor which is operated at about 450-about 700° F., under about 500 to about 2,200 psia $H_2$ partial pressure. Other hydrotreating conditions include about 0.5-about 5 LHSV and about 4,000 to about 10,000 SCF/Bbl GOR.

The hydrotreater effluent 110 is cooled and separated in a separator 50 into a liquid/paraffinic hydrocarbon stream 111, a water stream 112, and a gas stream 113. The processes to achieve this separation are well known to those having ordinary skill in the art, and include a high pressure hot separator, high pressure cold separator, and low pressure hot separators. The $C_5+$ paraffinic hydrocarbons, formed from algae oil hydrotreating, make up the composition of stream 111. Stream 112 includes the water co-product of the hydrodeoxygenation reaction. Water 112 may contain ions formed from dissolution of $CO_2$, $H_2S$, and $NH_3$ compounds. The water stream 112 may be directed to water treatment, or used as boiler feed water for producing a steam cracker steam 116.

The gas phase 113 is mainly unreacted hydrogen, propane, other light hydrocarbons, CO, $CO_2$, $H_2S$, and $NH_3$. In the embodiment shown in the drawing, the hydrotreater 40 is located in the olefin plant: 32, and the gas stream 113 is sent directly to the plant fuel gas header 123. In other embodiments, the gas stream 113 may be scrubbed to partially remove non-hydrogen components and recycled to the hydrotreater 40.

The paraffinic hydrocarbon stream 111 is then combined with a petroleum-based feed 114 to form steam cracker hydrocarbon feed 115. The petroleum-based feed 114 for a liquid feedstock steam cracker is typically naphtha but may also include heavier fractions such as gas oil. Although adding petroleum-based feedstock to the bio-derived paraffin 111 is not required, it is optionally included as shown in the FIG. 1 embodiment to provide the operators of the olefin plant 32 with feedstock flexibility.

Steam 116 is injected in the steam cracker hydrocarbon feed 115 as it enters the steam cracker 60. Steam cracker unit 60 is a conventional steam cracker designed for cracking petroleum fractions such as naphtha and gas oil, and operates at the conditions as described herein.

The quenched steam cracker effluent 117 is transferred to a fractionation train or fractionator 70. Therein the gas phase products are separated from the $C_5+$ liquid fraction 122, also referred to as pyrolysis gasoline. The gas phase products are compressed and fractionated into a hydrogen rich gas stream 109, ethylene 119, propylene 120, and C4 olefins 121. The separated methane and ethane are included in the fuel gas stream 118. The separation in the fractionator 70 is achieved using methods known to those having ordinary skill in the art. The separation equipment therein includes conventional and cryogenic distillation. Therefore, since such methods and mechanisms are well known to one of ordinary skill in the art, no further explanation of such methods and mechanisms need to be required herein.

The composition of hydrogen rich gas 109 in this embodiment is about 90 mol % H2, about 9 mol % methane, and about 1 mol % C2/C3 hydrocarbons. Hydrogen rich gas 109 is directed to the hydrotreater 40 for hydro-converting the algae oil feed 108 as described herein.

Pyrolysis gasoline stream 122, a C5+ hydrocarbon composition with olefin, aromatic, and naphthenic functional groups, is directed to a selective hydrogenation unit (not shown) to remove the diolefin gum formers, producing a bio-based gasoline blend stock.

Co-locating a bio-oil hydrotreater (the hydrotreater 40 and the separator 50) within the olefin plant 32 (the steam cracker 60 and the fractionator 70) provides a number of operational synergies. As observed, the hydrogen requirements for the hydrotreater 40 can be met by the hydrogen produced in the steam cracker 60 and recovered in the fractionator 70. Also, the bio-oil hydrotreater reaction is exothermic and heat generated therein (and optionally recovered by raising steam) may be used for the endothermic steam cracking energy (and steam) requirements.

The ethylene stream 119 is transported via pipeline to a polymerization unit 80 to produce LDPE pellets 124 for fabrication of plastic bags. The polymerization unit 80 is a conventional high pressure polyethylene process as described herein.

LDPE pellets 124 from polymerization unit 80 are transported to plastic bag fabrication unit 90. Bags are fabricated from polyethylene film, formed by extruding the polymer melt through a die with a circular slit of about 0.65 mm. The extruded thin-walled tube of polyethylene rises vertically and is filled with blown air, thus expanding the tube. Downstream, the tube is collapsed into polyethylene film and formed into bags. The bags produced are sold to various distributors and directly to stores and supermarkets. Some plastic bags are fabricated for use as trash bags, and purchased by consumers. It should be understood by one of ordinary skill in the art that although the example herein discusses the fabrication of plastic bags, any plastic product may be produced, as discussed herein, so long as the process functions in accordance with the present invention as described herein. After use, the plastic bags 125 are disposed and transported by waste management companies to land-fill 95 where the plastic bags, along with other polyolefin and non-polyolefin wastes, are stored underground. Because the plastic bags are non-biodegradable, they do not decompose into green house gases and effectively store carbon in the ground without polluting the environment. The $CO_2$ generated from combustion of coal 101 is thus sequestered in land-fill 95 while generating income for entities involved in the value chain.

In order to further illustrate the present invention, the following example(s) are given. However, it is to be understood that the examples are for illustrative purposes only and are not to be construed as limiting the scope of the subject invention.

Example 1

Steam Cracking of Biomass-Based Hydrocarbons

A biomass-based oil composition made of a blend of animal fats and spent vegetable oils was prepared. All biofeed components were obtained from Tyson Foods (Springdale, Ark.). The makeup of this blend is provided in Table 1.

TABLE 1

| Make-up of Bio Oil Blend | |
|---|---|
| Component | Amount (wt %) |
| Poultry Fat | 46 |
| Yellow Grease | 18 |
| Brown Grease | 18 |
| Floatation Grease | 9 |
| Grease from Prepared Foods | 9 |

The feed blend of Table 1 was subjected to acid wash pretreatment whereby phosphorus and metal contaminants were partially removed. The properties of the pretreated bio oil, including residual contaminants and fatty acid profile, are given in Table 2.

TABLE 2

Summary of analytical data on pretreated bio oil feed blend

Contaminants/Quality Analysis

| | |
|---|---|
| Ash (ppm wt) | 67.2 |
| Nitrogen (ppm wt) | 1006 |
| Sulfur (ppm wt) | 111 |
| Acid Value (mg KOH/g) | 129 |
| Karl Fisher Moisture (wt %) | 0.85 |
| Moisture and all Volatiles (wt %) | 1.30 |
| Insoluble impurities (wt %) | 0.04 |
| Unsaponifiables (wt %) | 1.03 |
| Peroxide value (meq/kg) | <0.2 |
| Thermal stability, AOM-20 hr (meq/kg) | 2 |

ICP-AES Analysis

| | |
|---|---|
| Calcium (ppm wt) | 14.5 |
| Iron (ppm wt) | 6.57 |
| Potassium (ppm wt) | 3 |
| Magnesium (ppm wt) | 0.532 |
| Sodium (ppm wt) | 6.79 |
| Phosphorus (ppm wt) | 8.28 |

Fatty acid profile

| | |
|---|---|
| C12:0 (wt %) | 0.1 |
| C14:0 (wt %) | 1.03 |
| C14:1 (wt %) | 0.17 |
| C15:0 (wt %) | 0.13 |
| C16:0 (wt %) | 20.5 |
| C16:1 (wt %) | 3.86 |
| C17:0 (wt %) | 0.35 |
| C17:1 (wt %) | 0.22 |
| C18:0 (wt %) | 8.56 |
| C18:1 (wt %) | 40.87 |
| C18:2 (wt %) | 19.49 |
| C18:3 (wt %) | 1.61 |
| C18:4 (wt %) | 0.28 |
| C20:0 (wt %) | 0.22 |
| C20:1 (wt %) | 1.08 |
| C20:2 (wt %) | 0.17 |
| C20:4 (wt %) | 0.23 |
| C22:0 (wt %) | 0.14 |

This was subjected to hydrogenation at 550-650 F and 1,600 psig over a sulfided nickel-mollybdenum catalyst in a pilot plant fixed-bed reactor. The liquid hourly space velocity through the reactor was 1 vol/vol/h with GOR of 7,500 SCF/Bbl. Residual elemental oxygen in the paraffinic hydrocarbon product was found to be below detection limit of 0.1 wt %. This paraffinic hydrocarbon was further refined using a Pt/Pd hydroisomerization catalyst. Hydroisomerization was conducted at 700-730° F. and 1,000 psig pressure at 0.8 LHSV and 3,000-4,000 SCF/Bbl. A product fraction was recovered for steam cracking. The composition of this biobased paraffinic hydrocarbon stream was measured via two-dimensional GC (GC×GC) analysis. The composition, broken down by carbon number and hydrocarbon type—paraffin (P), isoparaffin (I), olefin (O), naphthenics (N), and aromatics (A)—is provided in Table 3.

TABLE 3

PIONA weight percents determined by GC × GC analysis

| | P | I | O | N | A | SUM |
|---|---|---|---|---|---|---|
| 3 | 0.17 | 0.00 | 0.00 | 0.00 | 0.00 | 0.17 |
| 4 | 1.45 | 0.93 | 0.00 | 0.00 | 0.00 | 2.38 |
| 5 | 4.41 | 4.77 | 0.00 | 0.00 | 0.00 | 9.18 |
| 6 | 7.49 | 9.57 | 0.00 | 1.02 | 0.00 | 18.07 |
| 7 | 7.66 | 12.38 | 0.00 | 1.34 | 0.10 | 21.49 |
| 8 | 5.39 | 10.72 | 0.02 | 1.64 | 0.29 | 18.06 |
| 9 | 3.13 | 10.34 | 0.25 | 1.64 | 0.32 | 15.67 |
| 10 | 1.19 | 6.27 | 0.06 | 0.60 | 0.09 | 8.21 |
| 11 | 0.24 | 2.09 | 0.00 | 0.04 | 0.00 | 2.38 |
| 12 | 0.06 | 0.56 | 0.00 | 0.00 | 0.00 | 0.62 |
| 13 | 0.04 | 0.17 | 0.00 | 0.00 | 0.00 | 0.20 |
| 14 | 0.03 | 0.07 | 0.00 | 0.00 | 0.00 | 0.11 |
| 15 | 0.69 | 0.14 | 0.00 | 0.00 | 0.00 | 0.83 |
| 16 | 0.68 | 0.31 | 0.00 | 0.00 | 0.00 | 0.99 |
| 17 | 0.34 | 0.55 | 0.00 | 0.00 | 0.00 | 0.89 |
| 18 | 0.17 | 0.60 | 0.00 | 0.00 | 0.00 | 0.77 |
| SUM | 33.14 | 59.46 | 0.33 | 6.28 | 0.80 | 100.00 |

The bio-based paraffinic hydrocarbon composition of Table 3 was then steam cracked in a pilot plant steam cracker. The pilot plant steam cracker was designed to model performance of commercial units (Van Geem, K. M.; Reyniers, M.-F.; Marin G. B. *AIChE J.*, 50, 173-183, 2004). The steam cracker coil outlet pressure was controlled at 1.7 bar, with steam-to-hydrocarbon ratio of 0.45 w/w. The yields of the bio-derived olefins for selected coil outlet temperature (COT) experiments are presented in Table 4. Also included in Table 4 are comparable data for petroleum distillates with boiling ranges similar to the bio-based paraffinic hydrocarbon of this example.

TABLE 4

Product yields from steam cracking of biomass based paraffinic hydrocarbon and petroleum feedstocks of similar boiling range

| Feedstock | Medium range petroleum naphtha[a] | Atm. gas oil (petroleum)[a] | Bio-based Paraffinic Hydrocarbons - COT = 1,562° F. | Bio-based Paraffinic Hydrocarbons - COT = 1,535° F. |
|---|---|---|---|---|
| | Cracking yield | | | |
| Hydrogen and methane | 17.7 | 12.1 | 17.32 | 16.03 |
| Ethylene | 34.0 | 25.9 | 30.92 | 30.13 |
| Propylene | 15.7 | 16.2 | 17.59 | 18.94 |
| Butadiene | 4.7 | 4.6 | 5.165 | 5.282 |
| Total C$_4^-$ products | 76.4 | 63.6 | 84.04 | 85.0 |
| Pyrolysis gasoline | 18.8 | 18.4 | 14.79 | 14.65 |
| Pyrolysis fuel oil | 4.8 | 18.0 | 0.438 | 0.359 |
| Total | 100.0 | 100.0 | 99.3 | 100.0 |

Notes:
[a]Petroleum steam cracking data from Grub J. and Loser, E. Ullmann's Encyclopedia of Indusrial Chemistry, John Wiley; 2005.

As observed in Table 4, the bio-based paraffinic hydrocarbon cracks more completely to light olefins than do petroleum feedstocks (higher C$_4^-$ products and lower pyrolysis fuel oil). Yields of the main olefins (ethylene, propylene, and butadiene) are also generally similar or higher than petroleum feeds of similar boiling range.

From the above description, it is clear that the present invention is well adapted to carry out the objects and to obtain the advantages mentioned herein as well as those inherent in the invention. While presently preferred embodiments of the present invention have been described for purposes of this disclosure, it will be understood that numerous changes, variations, modifications and additions to this invention may be made which will be readily apparent to one skilled in the art and such modifications and additions would be fully within the scope of the invention, and which are accomplished within the spirit of the invention disclosed and claimed.

What is claimed is:

1. A method for sequestering carbon dioxide, comprising the steps of:
converting biomass into paraffinic hydrocarbons,
steam cracking the paraffinic hydrocarbons into olefins; and
polymerizing the olefins into non-biodegradable polyolefins.

2. The method of claim 1 wherein the paraffinic hydrocarbons are produced by gasification followed by Fischer-Tropsch conversion.

3. The method of claim 2 wherein the biomass is wood chips.

4. The method of claim 1 wherein the paraffinic hydrocarbons are produced by hydrotreating of fatty acids and/or fatty acid esters.

5. The method of claim 4 wherein the fatty acids and/or fatty acid esters are oils from plants.

6. The method of claim 4 wherein the fatty acids and/or fatty acid esters are fats from animals.

7. The method of claim 4 wherein the fatty acids and/or fatty acid esters are oils from algae.

8. The method of claim 7 wherein the algae are grown in ponds and/or photo-bioreactors with $CO_2$ supplied from stationary emission sources.

9. The method of claim 8 wherein the stationary emission source is a coal-fired power plant.

10. The method of claim 1 wherein the olefins comprise of ethylene, propylene, butenes, and butadiene.

11. The method of claim 1 wherein bio-derived hydrogen is produced as byproduct of steam cracking.

12. The method of claim 1 wherein bio-derived pyrolysis gasoline is produced as byproduct of steam cracking.

13. The method of claim 12 wherein the pyrolysis gasoline is used as motor gasoline blend stock.

14. The method of claim 13 wherein the pyrolysis gasoline is hydrogenated prior to use as motor gasoline.

15. The method of claim 1 wherein bio-derived fuel gas is produced as byproduct of steam cracking.

16. The method of claim 15 wherein the bio-derived fuel gas is supplied to the steam cracker furnace.

17. The method of claim 1 wherein the pyrolysis fuel oil yield is less than 1 wt % of the bio-derived paraffinic hydrocarbon.

* * * * *